US005707809A

United States Patent [19]

Halverson et al.

[11] Patent Number: 5,707,809
[45] Date of Patent: Jan. 13, 1998

[54] AVIAN SEX IDENTIFICATION PROBES

[75] Inventors: Joy Halverson; Jan Dvorak, both of Davis, Calif.

[73] Assignee: The Perkin-Elmer Corporation, Foster City, Calif.

[21] Appl. No.: 634,331

[22] Filed: Apr. 12, 1996

Related U.S. Application Data

[63] Continuation-in-part of Ser. No. 194,131, Feb. 9, 1994, Pat. No. 5,508,165, which is a continuation of Ser. No. 947,100, Sep. 17, 1992, abandoned, which is a continuation of Ser. No. 585,915, Sep. 21, 1990, abandoned.

[51] Int. Cl.$^6$ .............................. C12Q 1/68; C12P 19/34; C07H 21/04
[52] U.S. Cl. ..................... 435/6; 435/91.2; 536/24.3; 536/24.31; 536/24.33
[58] Field of Search .................... 435/6, 91.2, 810; 536/24.3, 24.31, 24.33

[56] References Cited

U.S. PATENT DOCUMENTS

| 5,215,884 | 6/1993 | McGraw, III | 435/6 |
| 5,266,317 | 11/1993 | Tomalski et al. | 424/93 T |
| 5,508,165 | 4/1996 | Halverson et al. | 435/6 |
| 5,530,186 | 6/1996 | Hitz et al. | 800/205 |
| 5,576,176 | 11/1996 | Adams et al. | 435/5 |

FOREIGN PATENT DOCUMENTS

| 63-258580 | 10/1988 | Japan . |
| 63-258581 | 10/1988 | Japan . |

OTHER PUBLICATIONS

Weeks et al., Proc. Natl. Acad. Sci. USA 84, 2798–2802 (1987).
Dvorak et al., J. Hered. 83(1), 22–25 (1992).

*Primary Examiner*—Kenneth R. Horlick
*Attorney, Agent, or Firm*—Scott R. Bortner

[57] ABSTRACT

Avian nucleotide sequences for use as sex specific markers are provided. Probes or primers derived from the sequences find use in defining the sex of a bird, by producing hybridization patterns or amplification products that are sex-specific. For a given avian species the probes may hybridize to both Z and W chromosomes so as to differentiate between the two chromosomes on the basis of restriction fragment length polymorphisms. Alternatively, the probes may hybridize exclusively to one of the two sex chromosomes in some species. The sequences taught are also useful for the isolation of other nucleotide sequences that are sex specific markers.

23 Claims, No Drawings

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 959 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
AACAGCATCT GATGCTGCAC CCCTTCAGTA TCTGGCTCCC TACTCAGGCT GCTCCATGGG      60

GGAATACTTC AGAGACAATG GGAAACATGC ATTGATCATC TACGATGACT TGTCCAAACA     120

GGCTGTTGCC TACCGTCAGA TGTCTCTGCT GCTGCGTCGT CCGCCTGGCC GTGAAGCTTA     180

CCCAGGTGAT GTGTTCTACC TGCACTCTCG CCTGCTGGAG AGAGCAGCTA AAATGAATGA     240

TTCCTTTGGA GGAGGCTCTC TGACTGCTTT GCCCGTCATT GAAACTCAGG CTGGTGATGT     300

GTCTGCTTAC ATTCCAACCA ATGTCATCTC CATCACTGAT GGACAGATCT TCTTGGAAAC     360

TGAACTGTTC TACAAAGGTA TCCGTCCAGC CATCAACGTT GGTCTGTCTG TGTCCCGTGT     420

GGGTTCTGCT GCTCAGACCA GGGCAATGAA ACAGGTGGCT GGTACCATGA AGCTGGAGCT     480

GGCTCAGTAC CGTGAAGTGG CTGCCTTTGC TCAGTTTGGG TCTGATTTGG ATGCTGCCAC     540

ACAACAGCTG CTGAATCGTG GTGTGCGTCT GACAGAGCTC CTGAAACAAG GACAGTATGT     600

TCCCATGGCT ATTGAGGAAC AGGTTGCAGT CATCTATCGT GGTGTAAGAG GTCACTTGGA     660

CAAGCTGGAG CCCAGCAAAA TCACTAAATT TGAGAGTGCT TTCCTGGCTC ATGTACTGAG     720

CCAGGACCAG GCCCTCCCTC TCCACCATCA GGACTGAAGG GAAGATCTCT GACCAGACGG     780

AAGCTAAGCT GAAGGAAATA GTCACAAATT TCCTATCTAC TTTTGAGGCA TAAACTCATT     840
```

```
ATCTGTTCAA ACAGACCAGG CTGTTTTTGT TGTTACGTGC TTTGCCTCCA TCAAAGACCT      900
AAACGTATCG AGTGCTTGAA TGTACAGATC TCACTGAGAA TAAAAGTTTC CATGTAAAA       959
```

( 2 ) INFORMATION FOR SEQ ID NO:2:

( i ) SEQUENCE CHARACTERISTICS:
    ( A ) LENGTH: 1899 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:2:

```
GCGGCCGCTC TAGAACTAGT GGATCCCCCG GGCTGCAGGA ATTCGGCACG AGCGGCAGAG      60
ATCCTCTGTC CGTTTCAGTC TTGCATGCGA TCGCTGTTAC TAACAGTATG TTTTCCGCCC     120
GCGTTCGTGC CGCCTTTGCT CGCTCCGTAC CACGGCAAGG CGGGCTGATT TCCAGAAATA     180
CCTTGGGTGT AGCATCCATT GCTGCAAGAA ACATCCATGC CTCCAAATCA CATTTTCAGA     240
GAACTGGCAC TGCTGAGGTA TCCTCTATTC TTGAGGAACG CATTTGGGA  GCCAACACCT     300
CTGCTGAACT TGAGGAAACT GGCCACGTGC TCTCAATTGG TGATGGTATT GCCCGTGTGT     360
ATGGCCTAAG AAATGTCCAA GCAGAAGAAA TGGTAGAGTT TTCTTCTGGC GTGAAGGGAA     420
TGTCCTTGAA CTTGGAGCCT GACAACGTTG GTGTTGTTGT GTTTGGTAAT GACAGACTGA     480
TCAAGGAAGG GGATGTTGTG AAGAGAACTG GTGCTATTGT GGATGTTCCA GTTGGAGAAG     540
AGCTGCTGGG CCGTGTTGTA GATGCCCTGG GCAATCCAAT TGATGGGAAG AGTTCTTTTA     600
CATCTAAAAG CGTAGAAGAG TTGGCTTAAA GGCCCTGGC  ATCATTCCA  GAATCTCTGT     660
GCGGGAACCT ATGCAGACTG GTATTAAGGC TGTGACAGCT TGTGCCCATT GGTCGTGGCC     720
AGCATGAGCT GATCATTGGT GACAGGCAGA CTGGAAAACT TCAATTGCAA TTGACAATAA     780
TCAACCNAAA AACGATTTAA TGATGGAGTA GATGAGAAAA GAAGTTGTAC TGTATCTACT     840
GTATCTATGT TGCTATTGGC CAGAAGAGAT CTACTGTTGC TCAGTTGGTG AAGAGGCTCA     900
CTGATGCAGA TGCCATGAAG TACACAATTG TGGTGTCTGC CACAGCATCT GATGCTGCAC     960
CCCTTCAGTA TCTGGCTCCT TACTCAGGCT GCTCCATGGG GGAATACTTC AGAGACAATG    1020
GAAAACATGC ATTGATCATC TATGATGACT TATCCAAACA GGCTGTTGCC TATCGTCAGA    1080
TGTCTCTGCT GCTGCGNCGT CCGCCTGGCC GTGAAGCTTA CCCAGGTGAT GTGTTCTACC    1140
TGCACTCTCG CCTGCTGGAG AGAGCAGCTA AATGAATGA  TTCCTTTGGA GGAGGCTCTC    1200
TGACTGCTTT GCCCGTCATT GAAACTCAGG CTGGTGATGT GTCTGCTTAC ATTCCAACCA    1260
ATGTCATCTC CATCACTGAT GGACAGATCT TCTTGGAAAC TGAACTGTTC TACAAAGGTA    1320
TCCGTCCAGC CATCAACGTT GGTCTGTCTG TGTCCCGTGT GGGTTCTGCT GCTCAGACCA    1380
GGGCAATGAA ACAGGTGGCT GGTACCATGA AGCTGGAGGT GGCTCAGTAC CGTGAAGTGG    1440
CTGCCTTTGC TCAGTTTGGG TCTGATTTGG ATGCTGCCAC ACAACAGCTG CTGAATCGTG    1500
GTGTGCGTCT GACAGAGCTG CTGAAACAAG GACAGTATGT TCCCATGGCT ATTGAGGAAC    1560
AGGTTGCAGT CATCTATGCT GGTGTAAGAG GTCACTTGGA CAAGCTGGAG CCCAGCAAAA    1620
TCACTAAATT TGAGAGTGCT TTCCTGGCTG ATGTACTGAG CCAGGACCAG GCCCTCCCTC    1680
TCCACCATCA GGACTGAAGG GAAGATCTCT GACCAGACGG AAGCTAAGCT GAAGGAAATA    1740
GTCACAAATT TCCTATCTAC TTTTGAGGCA TAAACTCATT ATCTGTTCAA ACAGACCAGG    1800
CTGTTTTTGT TGTTACGTGC TTTGCCTCCA TCAAAGACCT AAACGTATCG AGTGCTTGAA    1860
```

TGTACAGATC TCACTGAGAA TAAAAGTTTC CATGTAAAA                                              1899

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:3:

GATAGGCCAG CGTGGTATAA                                                                    20

( 2 ) INFORMATION FOR SEQ ID NO:4:

( i ) SEQUENCE CHARACTERISTICS:
        ( A ) LENGTH: 707 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:4:

CTGTCTCTCT CTCTGATCTC TGTCAGAGAC CTCAAAGGGG TCTCTGAGGA TTCACTGTTC        60
TCGGATGCAC AGTATAATGA CCACTCTCAC CCTTTTCCTT GAGGAATCTT CTACAAGAGG        120
CATAATCTTA GTGTGTTTAT CAATATCAGC CTCATTATTC CAAAAGTGGG CAGGGATCCT       180
TTCTGATGGG CAGACACATG TCCTATTGCA ATTGGTCGAG ATTTTGCATG TCTCAGGATT       240
TGTTGCCATA TCTCCTTTCC CCAAATGTCC TGGTTATTTA CCTGCCAATT ATTTCTTTGC        300
CAATTCCTCA ACCATTGTGT GGTTCCCGCC CAGACAGCAT AGGAGTCGGT GTAAATAGTA       360
CTAGCTCCAG CTTCTAAAGC CATTAAAATG GCTTGTAGTT CAGCCAGTTG GGCAGACCCC     420
CAATTGGGT GGTTATGACT TGTCAATTAG CCACTGACAC AGCAGTAGCA GTTCCTAACC        480
ATTTGCCCTC ACATCTCTTG GCAGACCCAT CAGTAAGCCA TACCCCTTTG GGTCATTGAG       540
GATCAAATTT GGGTACTTCA CTTATTGGGG AGTCAGGTTC CTCCCCATAT TCTTTGGACA     600
TTCCTATTCT CTGGACTTCT TCAGTTAGCT TCCCTTCACT TGGACTCTCA TTGCCTTCTG       660
CTCTAGAGTG AAGATACAAG GGCGGCCGCT CTAGAACTAG TGGATCC                                 707

( 2 ) INFORMATION FOR SEQ ID NO:5:

( i ) SEQUENCE CHARACTERISTICS:
        ( A ) LENGTH: 1236 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:5:

GGTGACTGTG CTAGCTAATA ACTACGAAAG AGCTGGACTT CTCCTTTCCA GCTCTTAGCT       60
ATGTTTTAGA AGAAAGCAGC ATTTGCGAGT GTATTCTGGA CAGAGAGAGA TTTTGCCAAA       120
AGGTAATTAC ATATAGTCTG GGATATTACC TACCTAGTAG AGGGACTCTG TAAGGGAGTT     180
TAGACAGAAG ACTTCTGGCT GAATATCAAA GTTAGGACCC ACATATGAAA CTTTACCTGA       240
GGTTCTTGAC AGCCACCAGA AAAATAGAGA CTTACCACGC ATTTGGAAGA TTTTAAGACT       300

-continued

```
AAAAGAAAAC TGGAGACATT TAAGGAATTT TGTCAAAGTT TTAAGGATGT CAGCACTGGA      360
GTTGAGCATG TAATTCAACT GAAATCCCAC GCTAGATACA CAGAAACTTT GTCTGTCTGT      420
CTGTCTCTCT CTCTCTCATC TGGCCCTACG GTTGTCAGGA GTCTTCAGTA AAACAGAAAA      480
TTAGACCCCA ACTTACCAAA TCCTAGAGAA TCATTTCAC  AGATGTACTA TCTCTTCTCT      540
CAGTGAATGA TTTTTTTTT  TTGAGCAACC TCAGAAATGT GCTGTGCAAA CATGTATTTC      600
TAGCTGTTAC TCCTGACAGG CTAAATCTGG AGGCATACAT ACAAATGTCT GTGGGATTTC      660
TACATTTGCA ATCATCTTAG TTATTTGAG  CTAAGTAATT TTTGGCCACA TTACAGTTCA      720
AGTTAACTGA TCTAGAAGCT GGGCCTGCAC TATTGCAGAT CTGGGCAGAG GTTAAGGGAG      780
GGAGCTGCAG AGGGGTTATA TGAAGGGTAG AGGTTAGGCT CAGCTTTCCA TTTTTCCCCT      840
TCTCCCATCT TCCTCTTCAT TCAGAGTTGA AATCCTCGAC TGATGTAGGG TTTATTTGTC      900
CCTGATCTCA TGCTTTCATT TATTTTAAT  GCTTTATAA  GTGGGAAGT  GTGATGATGG      960
TATAACTGAA TAGAATAGCC AAGGATATTG CGCTCTAGGG GCATAAAATG TGAACAGAGG     1020
TATGATCTAA TCTGTTTCA  TAGAAAAAAT CACAAGTCTG GGTTACTGA  GTTGTTGAAC     1080
TTTTACATAT TTGATAAACT AAAATTAAAT AAAATTATGT ATGAGTAATG GTAAAAACTC     1140
TCTTTTTTAG GTCTGTTTCT GCTCAGAGTA TTATTATCTG CTTCATTAGG AAGCTGGTCA     1200
ATAGTCTGAG ACTTGTCCAC AGTCACCACA GTCACC                               1236
```

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:6:

```
GTGTCTGCCA CAGCATCTGA TG                                                22
```

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:7:

```
GACAGACAGA CAGACA                                                       16
```

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:8:

```
CCTTGTATCT TCACTCTAGA                                                   20
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:9:

TCTCTGAGGA TTCACTGTTC                                                                                             20

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:10:

TGTATCTAGC GTGGGATTTC AGTTG                                                25

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:11:

GGTGACTGTG GTGACTGTGG ACAAG                                                25

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:12:

GGTGACTGTG CTAGCTAATA ACTACG                                              26

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:13:

GTATCTATGT TGCTATTGGC                                                                          20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:14:

CAGAGACATC TGACGATAGG          20

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:15:

GCTGGGCTCC AGCTTGTCC          19

( 2 ) INFORMATION FOR SEQ ID NO:16:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:16:

GCTGGTACCA TGAAGCTGG          19

AVIAN SEX IDENTIFICATION PROBES

CROSS REFERENCE TO RELATED APPLICATIONS

This application is a continuation-in-part of application Ser. No. 08/194,131, filed Feb. 9, 1994, now issued as U.S. Pat. No. 5,508,165, which is a continuation of application Ser. No. 07/947,100, filed Sep. 17, 1992, now abandoned, which is a continuation of application Ser. No. 07/585,915, filed Sep. 21, 1990, now abandoned.

INTRODUCTION

1. Technical Field

The field of this invention is DNA sequences having polymorphisms that make them suitable for sex identification in avian species, and methods for using such sequences.

2. Background

While the genetics and biochemistry of sex determination in mammals has been the subject of extensive scientific investigation, similar studies have not been carried out with respect to birds. This is surprising in view of the commercial importance of numerous avian species, e.g. chickens and turkeys. It is of interest to provide research tools useful for deciphering the complex process of genetic sex determination in birds. Sex-specific genetic markers are of particular interest. Such markers may be used to sexually identify immature birds prior to the development of gender specific morphological differences. Early sexual identification is an important consideration when breeding those birds that become sexually mature prior to or without the development of external sexual characteristics. Accordingly, there is interest in providing methods for preventing undesired matings by permitting gender identification (and gender separation) prior to the development of sexual maturity. Genetic sexual identification is also useful in the breeding of rare bird species with unidentified secondary sexual characteristics; captive breeding programs may thus be effectively organized.

Sex chromosomes, as opposed to autosomal chromosomes, differ with respect to one another in size and genetic composition. Thus, some regions of one sex chromosome contains genes which have no corresponding allele on the other sex chromosome. One of the principal ways in which the sex chromosomes of birds differ from man and other mammals is that the female bird is the "heterogametic" sex, having Z and W sex chromosomes. In mammals, the male is the "heterogametic" sex, having both X and Y chromosomes whereas the female is "homogametic".

To map genes whose manifestations are recognized only in the whole organism, the standard approach relies on identifying linkage between the trait and a genetic marker whose map position is already known. The most abundant and generally useful class of markers in the human genome are DNA sequence polymorphisms—either restriction fragment length polymorphisms (RFLP's) or other DNA polymorphisms that can be detected by hybridization with specific probes or by amplification using specific primers.

Marker probes consist of polynucleotide sequences that specifically hybridize to a region of the chromosome. These chromosomal regions of hybridization are revealed to be polymorphic between individuals of the same species when the chromosomal DNA is digested by restriction endonucleases and analyzed by hybridization analysis. Different alleles are distinguished from one another on the basis of the hybridization banding patterns produced after size separation. Genetic linkage analysis between markers and uncharacterized genes has proven to be a useful technique for isolating and mapping uncharacterized genes of interest. Although such markers have most frequently been used to identify the chromosomal disruptions responsible for genetic diseases, it is also of interest to use these markers in deciphering other complex genetic regulatory questions, such as sexual development in animals.

It is of interest to provide genetic makers suitable for the identification of DNA regions that are diagnostic of the sex of the bird. The DNA regions may be common to the Z and W chromosomes, such that polymorphisms unique to each sex chromosomes may be detected; or the DNA region may be unique to one of the sex chromosomes, so that the amount or presence of the marker will determine the sex of the bird. Such genetic markers permit the identification of the chromosomally specified sex of an individual bird based on analysis of a DNA preparation derived from the bird.

Relevant Literature

Halverson et al. (1985), A new method of avian sex determination-identification of the W body by C-banding of erythrocytes. *Proceedings of the Annual Meeting of the Association of Avian Veterinarians*. Boulder, Colo.

Halverson and Rauen (1988), The molecular approach to poultry breeding. *Proceedings of the Thirty-seventh Western Poultry Disease Conference and Molecular Biology Workshop*. Davis, Calif.

Japanese patents no. 63258580 and 63258581.

SUMMARY OF THE INVENTION

Avian nucleotide sequences useful as a source of probes and primers are provided. Primers and probes derived from these sequences, Tsex and other sequences, are used for sex identification of many avian species. Procedures are given for using the sequences to sexually identify individual birds. For example, in a given avian species, the probe may hybridize to both Z and W chromosomes, allowing for differentiation between the two chromosomes on the basis of length polymorphisms. Alternatively, the probe may hybridize exclusively to one of the two sex chromosomes, thus permitting gender identification on the basis of sex-specific hybridization intensity. The probes provide a means for identifying the gender of a bird without reliance on morphological characteristics. The probes also find use in recovering and identifying nucleotide sequences homologous to Tsex and other sex-specific nucleotide sequences, which may be genetically linked to genomic Tsex or Tsex-homologous sequences.

DESCRIPTION OF THE SPECIFIC EMBODIMENTS

Novel nucleic acid sequences and methods for using the sequences are provided for determining the chromosomally specified sex of individual birds. The method is based on the ability of probes or primers derived from the nucleic acid sequences to hybridize with sequences from the sex chromosomes of birds being analyzed for sexual identification. The nucleic acid sequences provided for, namely Tsex (SEQ ID NO:1; SEQ ID NO:2; SEQ ID NO:3), Osex (SEQ ID NO:4), Esex (SEQ ID NO:5) complements, derivatives thereof, and equivalent sequences, are homologous to nucleic acid sequences present on both or one of the Z and W chromosomes of most birds tested. However, there do exist arian species in which Tsex-homologous sequences are only present on one of the two sex chromosomes.

As used herein, the term homologous when applied to nucleic acid sequences intends nucleic acid sequences capable of hybridizing to each other at a stringency of at least about 25° C. below the $T_m$ ($T_m$ is the temperature at which about half the nucleic acid strands are denatured). In referring to "Tsex homologous sequences" it is intended to include the Tsex sequence itself. Various hybridization protocols may be used with Tsex-derived probes. See *Molecular Cloning: A Laboratory Manual*, second edition (1989), Sambrook et al., Cold Spring Harbor Laboratories Press, Cold Spring Harbor, N.Y., for examples of such protocols.

The subject invention permits the identification of the chromosomally specified sex of a given bird based on a hybridization analysis of genomic DNA extracted from the individual bird being gender tested. The Tsex sequence is useful for sex identification in a wide variety of bird species. Suitable birds for chromosomal identification by Tsex hybridization have Tsex-homologous sequences present on one or both sex chromosomes.

The subject invention provides a means for identifying the gender of avian species without relying on morphological sexual characteristics. The subject invention is used to identify the sex of birds when secondary (external) sexual characteristics are absent or unknown. The identification of sex in the absence of secondary sexual characteristics is useful, because in commercial breeding operations it is advantageous to separate sexually mature birds from one another in order to prevent undesired matings. Sex identification is also useful for raising poultry more efficiently, prevention of fighting, etc. This separation may be difficult to achieve because some avian species become sexually mature prior to or without the development of obvious external sexual differences. By providing for a simple and reliable means of gender identification prior to the development of external sexual characteristics in birds, the subject invention finds use in commercial bird breeding. By permitting the creation of breeding pairs, the subject invention provides a rational means of breeding rare birds.

Gender identification is critical in establishing captive breeding of sexually monomorphic avian species such as ostrich. Early sex identification is important, especially when birds become sexually mature prior to development of secondary sexual characteristics. In addition, it is valuable to obtain gender information for ostriches in particular at a young age because even juvenile birds are currently quite costly. If the sex of the birds can be established early, then the purchasers can have full confidence that they have procured birds of the desired gender, even if the birds are far from sexual maturity. Sequences useful for sex determination of ostriches (Osex, SEQ ID NO:4) and emus (Esex, SEQ ID NO:5) am provided. Where Tsex sequences have not been useful for sexual identification of Ratite sp., the Osex or Esex sequences are then used for sex identification.

Oligonucleotide primers from the subject sequences may be used with amplification reactions, e.g. polymerase chain reaction (PCR), ligase chain reaction, etc., to amplify fragments from genomic avian DNA. The Tsex intron sequence has been found to be useful in a number of different species. Sequencing of the Tsex intron from Z and W chromosomes has resulted in the identification of sequence differences specific to the sex chromosomes. These differences are used to design oligonucleotide primers that specifically identify the gender of various bird species. Examples of useful intron sequence differences are sequence differences between the W and Z chromosomes allowing specific amplification of fragments from the W chromosome; differences between the Z and W chromosome in the size of the intron resulting in amplified fragments of different sizes; and sequence differences between the Z and W chromosomes that allow the amplified fragment to be differentially digested with a restriction enzyme. The amplification primer SEQ ID NO:3 is exemplary of an intron sequence that is specific to the W chromosome of many arian species. In combination with an oligonucleotide primer of SEQ ID NO:2, for example SEQ ID NOs:6 and 13, amplification produces a detectable fragment in females only. The presence of the female specific amplification product may be detected by measuring incorporation of labeled nucleotides, e.g. TCA precipitation, etc., by detecting a change in absorbance ($A_{240}$; $A_{260}$); detecting a change in the ability of the sample to bind DNA intercalating agents, or by size fractionation of the amplification products, e.g. gel electrophoresis, capillary electrophoresis, etc.

Primers from the Osex and Esex sequence can be used to generate an amplified DNA in the PCR that is specific to female ostriches or emus. When the PCR is performed at low stringency, as described in the examples, additional DNAs common to male and female are also amplified. These fragments act as internal controls for the PCR, so that reactions containing male DNA can be distinguished from failed reactions. Internal controls can also be produced with a high stringency, multiplexed PCR, i.e. where multiple sets of primers are present in the reaction. Where low stringency PCR is used, the amplification products may be size fractionated for detection of the female specific product. Fluorescent detection can also be used to detect the amplification product, by incorporation of a detectable label in the amplification reaction. Suitable labels include various fluorochromes known in the art. The use of different fluorochrome dyes e.g. fluorescein isothiocyanate (FITC), rhodamine, Texas Red, phycoerythrin, allophycocyanin, 6-carboxyfluorescein (6-FAM), 2',7'-dimethoxy-4',5'-6-carboxyfluorescein (JOE), 6-carboxy-X-dichloro-6-carboxyfluorescein (JOE), 6-carboxy-2',4',7',4,7-rhodamine (ROX), 6-carboxy-2',4',7',4,7-hexachlorofluorescein (HEX), 5-carboxyfluorescein (5-FAM) or N,N,N',N'-tetramethyl-6-arboxyrhodamine (TAMPRA), can be used to differentiate W specific amplification products from internal controls.

Hybridization probes derived from the subject sequences find a variety of uses in addition to their use in sexual identification. Such hybridization probes may be used to isolate homologous sequences. Such isolation is achieved by screening recombinant DNA libraries prepared from avian DNA (or cDNA) from species other than turkey (the Tsex sequence being derived from a turkey cDNA). In addition, these probes may be used to isolate full length cDNAs and genomic sequences. Similarly, these hybridization probes may also be used in chromosome walking or jumping techniques to isolate coding and noncoding sequences chromosomally proximal, though not necessarily adjoining, to homologous sequences. Probes may be employed with chromosome walking and jumping techniques as described in a number of commonly available publications, e.g. Sambrook et al., supra.

Additional uses of the subject invention are found in the isolation of sex determination mutations in avian species. Mutations affecting sex determination have found use in manipulating progeny phenotype in the controlled breeding of numerous animals (e.g. linked X chromosomes, autosomal-sex chromosome translocations). The subject invention facilitates the discovery of sex determination mutants by allowing investigators to determine the sexually specified genotype of mutant birds with questionable sexual morphology.

The Tsex sequence was obtained from a cDNA library prepared from turkey embryonic poly(A)$^+$ mRNA. The short Tsex sequence, SEQ ID NO:1, is 959 base pairs in length, shown in the sequence listing. The extended Tsex sequence, which includes SEQ ID NO:1, is shown in the sequence listing as SEQ ID NO:2. Nucleotides 1 to 941 of SEQ ID NO:2 are not present in SEQ ID NO:1.

The subject sequences may be used for the production of a variety of nucleic acid hybridization probes. Such hybridization probes find use for many purposes, including sex identification in birds and the isolation of homologous sequences from a genetic library. Probes may be either single or double stranded, either RNA or DNA. Probes may be produced by in vitro or in vivo synthesis, or a combination thereof. Methods of in vitro probe synthesis include organic chemical synthesis processes or enzymatically mediated synthesis, e.g. by means of SP6 RNA polymerase and a plasmid containing one of the subject sequences under the transcriptional control of an SP6 specific promoter, by PCR, etc. Usually, hybridization probes will have a specific complementary sequence of at least about 18 nucleotides, more usually at least about 35 nucleotides and preferably greater than about 50 nucleotides and, more preferably having substantially the complete sequence of SEQ ID NO:1; SEQ ID NO:2; SEQ ID NO:4 or SEQ ID NO:5. Probes may have either complete or partial sequence identity to the sex specific sequence. Probes having partial identity will usually have less than 20% mismatch, and preferably less than 10% mismatch with the sex specific sequence.

Sequences will be also be selected to generate amplification primers. The exact composition of the primer sequences are not critical to the invention, but they must hybridize to the sex specific sequence under stringent conditions. Conditions for stringent hybridization are known in the art, for example one may use a solution of 5×XSSC and 50% formamide, incubated at 42° C. To maximize the resolution of size differences at the locus, it is preferable to chose a primer sequence that will generate an amplification product of at least about 50 nt, preferably at least about 100 nt. As described above, Tsex intron sequences are useful for amplification based sex determination. Algorithms for the selection of primer sequences are generally known, and are available in commercial software packages. The primers will hybridize to complementary strands of chromosomal DNA, and will prime towards each other. The primers will usually be at least about 18 nt in length, and usually not more than about 35 nt in length. Primers may be chemically synthesized in accordance with conventional methods or isolated as fragments by restriction enzyme digestion, etc.

When performing sex determination analysis using probes from one of the subject sex specific sequences, the probes are preferably hybridized against DNA preparations from birds of known sex in order to verify that the probes produce the desired sex-specific hybridization pattern. Similarly, when sexing previously untested species of birds, the sex-specific nature of the hybridization patterns produced with Tsex sequence derived probes are preferably verified by hybridization against birds of known sex.

Probes may be modified by conjugation to a variety of labels that allow for detection of duplex formation between the probe and its complementary target. Labels include radioactive isotopes, ligands, e.g. biotin, enzymes, fluorescers and the like. A wide variety of protocols for labeling probes and detecting duplexes formed between probes and their target hybridization sequences have been described in the literature. See for example, Berger and Kimmel, *Guide to Molecular Cloning Techniques* (1987) Academic Press Inc., San Diego, Calif.

Probe sequences may be joined to a variety of other nucleic acid sequences. Among these other nucleic acid sequences are vectors, such as plasmids, cosmids, phages, and the like. By joining the probe sequence to a vector sequence, probes may be conveniently created, expanded, stored, and modified.

Nucleic acid preparations suitable for hybridization analysis may be isolated from any portion of a bird's body containing substantially intact nucleic acids. Preferably, nucleic acid preparation sources are obtained without killing or injuring the bird and are easily removed from the test bird. Preferred sources of starting material will be feather pulp, blood, mature feathers, cell scrapings, feces, or the like.

Tsex-derived hybridization probes are used to determine the sex of an individual bird based on nucleic acid hybridization analysis. As previously discussed, hybridization analysis demonstrates that Tsex-homologous sequences am present on at least one, and usually both sex chromosomes of numerous avian species. For those species that have Tsex-homologous sequences present on both Z and W sex chromosomes, hereinafter called Tsex-double species, Tsex sequence derived hybridization probes are used to distinguish male from female DNA preparations on the basis of the presence of at least one additional hybridization band present in the female chromosomal preparations. For those bird species having Tsex-homologous sequences present on only one sex chromosome, hereinafter called Tsex-single species, the genetically specified sex of the bird from which the DNA was prepared is determined by employing a Tsex-specific probe and semi-quantitatively comparing the degree of hybridization of the probe to a sample with the degree of hybridization of the same probe to a standard of known sex.

Tsex-double species include, but are not limited to: turkeys, chickens, Canada geese, pheasants, zebra finches, lapwings, sandgrouse, murres, caiques (including: white-bellied and black-headed), macaws (including: blue & gold, scarlet, hyacinth, yellowcollar, hahns, greenwing, and military), red-bellied parrots, amazons (including: Mexican red-headed, orangewing, red lored, mitred, cherry-head, yellow-nape, and blue-front), cockatoos (including: rose-breasted, goffins, umbrella, mollucan, and sulfur-crest), lorries, cockatiels, budgerigars, rosellas, cranes, herons, ibis, crows, owls, storks, pigeons, doves, turacos, kingfishers, passerines, honeycreepers, parrots, african grey parrots, all conures, Brotogeris spp., Loridae spp., Pionus spp., Poicephalus spp., and Psittacula spp.

Tsex-single bird species include but are not limited to: Eclectus parrots, lovebird, hawks and eagles.

Some bird species are not amenable to sex identification with Tsex-derived probes with the restriction endonucleases currently employed, but may be capable of identification with an appropriate endonuclease. Tsex-derived probes hybridize to sequences on both the W and the Z chromosomes in these species; however, the hybridization patterns produced do not vary between the sexes. The only species tested that are not currently amenable to sex identification with Tsex-derived probes are ostriches, emus, penguins, albatross, pelicans, cinerous vultures, and Russell Griffon vultures.

Sex identification of ostriches may be performed with sequences derived from SEQ ID NO:4, and sex identification of emus from sequences derived from SEQ ID NO:5. The Osex and Esex sequences are employed to generate single locus RFLPs which are specific to females. When the RFLP is obtained using the enzyme described, an additional band common to males and females is observed; this band is useful as an internal control for the presence and quality of DNA in each lane.

One preferred method of sex identification by hybridization analysis requires the immobilization of target hybridization sequences onto a solid support. Avian sex identification employing the process of nucleic acid hybridization with the subject sex specific probes may utilize solid immobilization supports suitable for hybridization analysis with most generally recognized nucleic acid hybridization procedures. Suitable support membranes capable of binding nucleic acids include nitrocellulose, Nytran™, Zetaprobe™ and the like. A variety of protocols for immobilizing nucleic acids to membranes have been described in the literature. See for example, Berger and Kimmel, supra. The immobilization procedure may be mediated by capillary transfer, electrophoretic transfer, vacuum transfer and the like. The amount of genomic DNA transferred to the solid support membrane will generally be in the range of about 0.01 µg to 20 µg, preferably in the range of about 0.05–5 µg, per sample for analysis.

Chromosomal DNA preparations suitable for hybridization may be digested with restriction endonucleases prior to the transfer of the nucleic acids to an immobilizing support, usually after size separation where the sex is determined based on the difference in size of one or more fragments. Prior to immobilization, chromosomal DNA preparations from Tsex-double species must be digested with at least one restriction endonuclease, whereas chromosomal DNA from Tsex-single species are preferably, though not essentially, digested with at least one restriction endonuclease. Useful restriction endonuclease are selected for their ability to produce a sex-specific hybridization pattern when hybridized against the subject probes. Where restriction sites are present within the sex specific sequence, a number of fragments which bind to the probe may be produced. Digestion with suitable restriction endonucleases produces chromosomal fragments with sizes capable of being separated by electrophoresis.

When DNA preparations for gender determination analysis are subjected to restriction endonuclease digestion, the DNA preparations are size separated by electrophoresis, and transferred in situ from the gel electrophoresis separation medium to a nucleic acid binding support. Electrophoretic separation should proceed to a point where the degree of chromosome digest fragment separation achieved by electrophoresis is sufficient to separate chromosomal fragments from one another to an extent capable of being detected by hybridization analysis. Suitable gel electrophoresis separation media include agarose, polyacrylamide, mixtures thereof, and the like, at a concentration suitable for the separation of nucleic acid fragments to an extent sufficient to reveal size differences between the hybridizing DNA fragments. The in situ transfer of nucleic acids to a binding membrane may be achieved by any of the standard procedures for hybridization analysis. Exemplary, but not exclusive of such procedures are Southern blotting and electroblotting.

After immobilization to a solid support, the samples are hybridized against the subject hybridization probes. Duplexes formed between the labeled probe and the homologous sequences in the samples for analysis and any hybridization standards present are subsequently visualized by methods appropriate to the probe label.

When performing chromosomal sex analysis on Tsex-double species, male and female chromosomal DNA hybridization sex standards are optionally, although preferably, present. By hybridization standards, it is intended chromosomal DNA from an individual of known sex and of the same species as the individual undergoing sex determination analysis; the standard is also present in a quantity essentially the same as the DNA sample for analysis.

Male and female DNA samples from Tsex-double species may be distinguished from one another by the presence of at least one hybridization band found in the chromosomal preparation of one sex that is not found in preparations of the other sex. Frequently a plurality of bands of different sizes bind to the probe, and all that is required to distinguish the sex of the subject bird is that there be a band of a size characteristic of a particular sex, where the absence of the band is characteristic of the other sex. Furthermore, the intensity of the hybridization bands in common between male and female chromosomal DNA preparations have greater (usually approximately double) hybridization intensity in male derived samples because of the double dose of target DNA from the two Z chromosomes. Thus, by comparing DNA samples for analysis with each other, or comparing the samples with known male and female standards of the same species, the sex of the individual animal providing the DNA for analysis may be determined.

Sex identification in Tsex-single species is performed essentially the same as in Tsex-double species; however, the restriction endonuclease digestion and electrophoresis separation steps are optional (although preferably performed) rather than required as with the analysis of Tsex-double species. When analyzing Tsex-single species, all DNA samples for analysis and hybridization standards are necessarily present in approximately the same quantity so that the intensity of hybridization produced is accurately compared among samples and hybridization standards.

In Tsex-single species where Tsex-homologous sequences are only present on the Z chromosome, probe hybridization with chromosomal preparations from males displays greater (approximately double) hybridization intensity than probe hybridization with equal quantities of DNA from female members of the same species.

Tsex-derived probes also find use in isolating other sex-specific sequences. Since the Tsex probes that hybridize to the W and Z chromosomes are the same sequence, it is apparent that the sex-specific nature of the hybridization is attributable to chromosomal sequences other than Tsex itself (or Tsex-homologous sequences in species other than turkey). On the chromosome, Tsex-homologous sequences lie close to nucleic acid sequences that differ from one another in a sex-specific manner. These as yet unidentified sex-specific sequences may be detected by employing conventional library screening techniques, including chromosome walking (Bender et al. (1983) *J.Mol.Biol.* 168:17) and chromosome jumping (Poustka et al. (1987) *Nature* 325:323), to recover sequences proximal to Tsex homologous sequences, in which at least the first round of library screening employs a Tsex sequence derived probe. These library screening techniques are discussed at length in Berger and Kimmel, supra. and Sambrook et al., supra.

Genetic libraries for screening with Tsex derived probes may be prepared in plasmid, cosmid, or YAC (yeast artificial chromosome) vectors or the like. Portions of nucleotide sequences isolated in a first round of screening that are not homologous to Tsex may be labeled and used as probes for a second round of library screening. The process of repeatedly screening a library with newly isolated sequences may be repeated as desired so as to "walk" or "jump" down the chromosome. Progression down the chromosome from the Tsex homologous region may proceed in either direction. The region of the chromosome analyzed by "walking" techniques and the like may extend for a distance greater than 5000 kb to either side of the Tsex region (or Tsex-homologous region), however preferred distances for walking are in the range of about 100–1000 kb. Chromosomal regions of interest also include introns within the Tsex-homologous genomic sequence. Nucleotide sequences not homologous to Tsex that are isolated during "walking" may be screened for their ability to produce sex-specific hybridization patterns when used as hybridization probes. It is also of interest to engage in chromosome walking for the purpose of isolating sex-specific nucleotide sequences in those bird species that have non-polymorphic Tsex-homologous sequences on both the W and the Z chromosomes, e.g. penguins.

For an example of using Tsex to isolate additional sex-specific nucleotide sequences, consider the case of screening a turkey genomic library with a labeled Tsex DNA sequence as a probe. Plasmids from individual clones recovered in the screening may then be restriction mapped and regions of the recovered plasmids not homologous to Tsex isolated. The isolated regions are then labeled for use as probes in a second round of library screening. Sequences recovered from library screening may also be tested for use as sex-specific probes by labeling the newly isolated sequences and hybridizing the labeled sequences against Southern blots containing restriction digested genomic DNA from both male and female birds of the same species. Sequences that reveal sex-specific hybridization pattern polymorphisms find use in sex identification protocols similar to those employing Tsex-derived probes.

Besides using the nucleic acid as an identifier of sex, the expression product may also be used to identify sex. To the extent that the expression products of the two sequences differ as to epitopes, antisera or monoclonal antibodies may be prepared which will distinguish between the two alleles, when the Tsex or related gene is present on both chromosomes. Where the gene is only on one chromosome, the amount or presence of the protein will indicate the sex of the bird. Various immunoassays may be used to detect the proteins, using radioisotopes, enzymes, chromophores, fluorophores, chemiluminescers, or the like, as detectable labels.

Kits may be provided with probes and standards for determining the sex of birds. Thus, by carrying out the assay with the sample and having genomic DNA which may be processed in the same manner, the results may be compared directly. Thus, the kit would comprise one or more probes, usually one probe, generally labeled, and genomic DNA for one or both sexes of the bird of interest for processing in the assay and comparison with the sample DNA. Alternatively, a kit would comprise one or more pairs of amplification primers suitable for avian sex identification.

The invention now being generally described, the same will be better understood by reference to the following examples which are provided for purposes of illustration only and are not to be considered limiting of the invention unless so specified.

EXPERIMENTAL

EXAMPLE 1

CLONING AND CHARACTERIZATION OF TSEX

RNA Isolation. A cDNA library was prepared from poly A mRNA isolated from turkey embryos. All RNA isolation procedures and manipulations were performed in RNAse free laboratory articles. In order to remove RNAse contamination, glassware was baked at 180° to 190° C. overnight and plasticware was treated with a 0.2% diethylpyrocarbonate (DEPC) solution.

8.3 gms of 3, 4, and 5 day old turkey embryos were pooled together and placed in a lysis buffer (7 ml of buffer/1 gm tissue). The lysis buffer is composed of 4M Guanidinium isothiocyanate, 0.2M Tris pH 7.5, 0.01M EDTA, 5% β mercaptoethanol (w/v).

The tissue was homogenized in a Polytron™ homogenizer at setting "5" for 1 minute. The homogenate was strained through a cheese cloth and a myra cloth filter (a double layer in which the homogenate first passes through the cheese cloth). The filtrate was then centrifuged at 10,000×g at 25° C. for 10 minutes. The supernatant was removed and N lauryl sarcosine was added to a final concentration of 0.5%. Seven volumes of 4M LiCl were then added. The supernatant was then allowed to sit for 15–20 hours at 4° C. The solution was then centrifuged at 10,000×g for 90 minutes at 4° C. The supernatant was removed, and the pellet was resuspended in 100 ml of 3M LiCl. The solution containing the resuspended pellet was then centrifuged at 10,000×g for 60 minutes at 4° C. and the supernatant removed. The pellet was then dissolved in a solubilization buffer by vortexing. RNA solubilization buffer: 0.1% SDS, 0.01M pH 7.5 Tris, EDTA pH 8 0.5 mM (about 50 ml buffer/10 gm sample). The RNA was then extracted with an equal volume of phenol: chloroform: isoamyl alcohol (25:25:1) solution. The aqueous phase of the extraction was saved and a 3M potassium acetate solution was added to make a solution with a final concentration of 0.2 molar potassium acetate. 2.2 volumes of 95% ethanol were then added. The solution was dispensed into 30 ml Corex™ tubes. The Corex™ tubes were stored at −20° C. overnight. The tubes were then centrifuged at 10,000×g for 30 minutes at 4° C. The supernatant was removed and the pellet was washed with a 70% ethanol solution. The tube was allowed to drain and then subsequently dried in a vacuum oven for 20–60 minutes. The pellet was then resuspended in sterile deionized water.

Isolation of Poly A mRNA. Poly A mRNA isolated from the total embryonic turkey RNA preparation by oligo(dT)-cellulose was equilibrated with about 2 ml of loading buffer (loading buffer; 20 mM Tris pH 7.5, 0.1 mM EDTA, 0.5M LiCl, 0.1% SDS). The oligo (dT)-cellulose slurry was poured into a 1.0 ml siliconized Pasteur pipette (plugged with siliconized glasswool). The column was washed with 3 volumes each of (1) sterile deionized water, (2) 0.1M NaOH, 5 mM EDTA, (3) sterile deionized water. The column was washed with water until the column effluent had a pH of less than 8.0. The column was then washed with 5 volumes of loading buffer. An aqueous solution containing the total RNA isolated from turkey embryos was heated to 65° C. for 5 minutes. Equal volumes of 2×loading buffer was added to the RNA solution and the solution was allowed to cool to room temperature. The solution was then applied to the top of the oligo(dT)cellulose column. The column effluent was collected and heated again to 65° and reapplied to the top of the column. The column was then washed with 5 mls of loading buffer. 1 ml aliquots of column effluent were collected. 5 volumes of 0.1M LiCl buffer (20 mM Tris pH 7.5, 1 mM EDTA, 0.1M LiCl, 0.1% SDS) were then added to the column. The mRNA fraction was then eluted with 5 volumes of eluting buffer (lmM Tris pH 7.5, 1 mM EDTA, 0.05% SDS). 1.0 ml aliquots of column effluent were collected. The column was then rinsed with the deionized water, until the concentration of RNA in the effluent was approximately 0.

The $A_{260}$ of each column fraction was determined in order to measure RNA concentration. The fractions were then stored at $-70°$ C. in 70% ethanol and 0.2M potassium acetate.

cDNA Cloning. The embryonic turkey cDNA library was generated using the methods and vectors described by Alexander et al. (1987) "Dimer—Primer cDNA Cloning", *Methods in Enzymology* 154, Academic Press. The cDNA was cloned into the SstI site of pARC 7. Plasmid pARC 7 was digested with SstI and poly-dT tailed using terminal deoxynucleotidyl transferase. Isolated embryonic turkey mRNA was allowed to anneal to the poly-dT tails via the poly-A tails of the mRNAs. After annealing to the poly-dT tail primers, the first strand of cDNA synthesis was catalyzed using murine Moloney leukemia virus reverse transcriptase. The first DNA strand was then poly-dG tailed using terminal deoxynucleotidyl transferase. The modified vector bearing cDNA strands on both termini was then digested with the restriction enzyme BamHI. A BamHI linker with a poly-dC tail was then annealed to the poly-dG tail at 42° C. The mixture was then cooled, permitting the constructs to circularize through the annealing of the BamHI sticky ends. Circularization was completed by the use of T4 DNA ligase. The RNA strand still remaining in the construction was removed by mixing the RNA-DNA duplex with RNase H and replacing the RNA with DNA using DNA polymerase I. The remaining nick was then closed with T4 DNA ligase and the constructs were transformed into *E. coil* strain DH5α.

Isolation of pTsex (SEQ ID NO:1). Clones from the turkey embryonic cDNA library were selected at random and the plasmids within them prepared by a plasmid miniprep procedure (Birnboim and Doly (1979) *Nucleic Acids Research* 7:1513). The turkey embryonic cDNA library plasmids were then screened by digestion with either PstI or XbaI, resulting in the release of the insert portion of the plasmid, and subsequent separation of the vector from the insert by agarose gel electrophoresis. Clones bearing inserts of greater than about 400 base pairs were subjected to further screening.

Further screening was carried out by radioactively labeling the cDNA portion of the isolated clones and using the resulting radioactive probe to screen Southern blots containing restriction digested chromosomal adult turkey DNA from both male and female turkeys. Prior to radioactive labeling, the inserts from the clones for further analysis were subjected to digestion with either PstI or XbaI, followed by separation of the digestion fragments from one another by agarose gel electrophoresis. The plasmid insert was isolated from the gel by electroelution. The insert was then radioactively labeled by nick translation. Nick translation was performed by placing the following mixture in a 1.5 ml eppendorf tube: 0.5 µg of insert DNA, 2.5 µl of 10×nick translation buffer (500 mM Tris pH 7.8, 50 mM MgCl, 100 mM β mercaptoethanol, 100 µg/ml BSA), 2.5 µl 2 mM dTTP, 2.5 µl, 2.5 µl 2.0 mM dCTP, 5 µl dATP 3000 curies/mM $^{32}$p, 2 µl DNAse I (1U/100 µl), 1 U DNA polymerase I, $H_2O$ to 25 µl total volume. The mixture was incubated 75 minutes at 15° C. 8 µl 0.25 M EDTA was added, and the mixture was incubated 65° C. for 10 minutes to stop the reaction. 1 µ of 10 mg/ml sonicated salmon sperm DNA was then added in order to increase recovery of the probe. The unincorporated nucleotides were removed by gel filtration through a G-75 Sephadex column.

The $^{32}$p labeled inserts were then used as probes to hybridize with a Southern blot containing restriction digested chromosomal DNA prepared from turkey blood. Southern blots used for the screening of the embryonic turkey cDNA library contained chromosomal DNA from eight turkeys, four males and four females. 5 µg specimens of chromosomal DNA isolated from the blood of three male and three female turkeys were separately digested with BamHI and EcoR I. Also a single pair of chromosomal DNA preparations from male and female turkeys was digested with HindIII. The chromosomal digest fragments were separated by agarose gel electrophoresis and transferred to a Zetaprobe (BioRad) filter membrane by Southern blotting. All potential gender identification markers were tested against Southern blots containing this combination of restriction digested turkey chromosomal DNA.

The pre-hybridization solution (see section on hybridization conditions for the composition of this solution) was added to a polyethylene baggy containing the Southern blot and allowed to incubate at 65° C. overnight. The pre-hybridization solution was removed, and hybridization solution added. The hybridization solution was essentially the same as the pre-hybridization solution with the exception that the hybridization solution contained all of the probe labeled in the nick translation reaction (denatured at 95° C. for 10 minutes). The hybridization was allowed to proceed for 36 hours at 65° C.

After hybridization, the membranes were washed by the following procedure. The first wash was in a solution consisting of 1×SSC, 1% SDS, at 45° C. for 10–15 minutes. The blot was then washed in a solution of 0.1×SCC, 1% SDS, 0.1% sodium pyrophosphate, at 65° C. for 40 minutes. After washing, the blot was blotted dry on Whatman™ 3 MM paper, wrapped in saran wrap, and exposed to Kodak™ XAR X-ray film for three days. The X-ray film was subsequently analyzed for differences in the banding pattern between male and female chromosomal DNA preparations digested with the same restriction enzyme. The desired sex-specific probes should produce no variation in the banding patterns between DNA samples from members of the same sex.

The third embryonic turkey cDNA library clone tested by the above described procedure revealed a sex-specific hybridization pattern. Hybridization with this probe, named the Tsex sequence, with all three male turkey chromosomal DNA preparations digested with BamHI has revealed identical hybridization bands of 19.5 kb and 11.5 kb, whereas hybridization of pTsex with all three BamHI digested chromosomal DNA preparations from female turkeys resulted in the formation of hybridization bands with sizes of 19.5 kb, 13.5 kb, 11.5 kb, 7.3 kb, 6.4 kb and 5.5 kb.

EcoRI digested male chromosomal DNA probed with Tsex resulted in the formation of hybridization bands with sizes of about 13.5 kb, 3.9 kb and 3.4 kb whereas hybridization with EcoRI digested female turkey DNA resulted in the formation of hybridization bands with weights of about 13.5 kb, 9.1 kb, 3.9 kb, 3.4 kb and 2.3 kb. There was no variation in the hybridization patterns produced among the female DNA samples as well as among the male DNA samples.

Male chromosomal DNA digested with HindIII produced hybridization bands with weights of about 5.5 kb and 2.5 kb, whereas hybridization of chromosomal DNA resulted in the formation of hybridization bands with weights of about 6.5 kb, 5.7 kb, 5.3 kb, 4.4 kb, and 2.5 kb.

Blood Collection. Venous blood is collected by clipping a toenail sufficiently short that the blood vessel in the toenail (which usually ends in the distal quarter of the nail) is opened. After the blood has begun to ooze rapidly, a 20 µl Unopette™ pipette is held to the nail and blood is allowed to flow into the pipette quickly by capillary action. The other end of the Unopette™ fits onto the nozzle of a squirt bottle containing 70% ethanol. The ethanol is squirted through the pipette, washing the collected blood into a 2 ml polypropylene screw cap tube which is then capped. There should be no more than a 30 second delay between blood collection and mixing of the blood with 70% ethanol. The blood is now preserved and will be useful for DNA isolation during several weeks of storage at room temperature.

Blood can also be collected by venipuncture if desired. The wing vein (brachial vein) and jugular vein are preferred. The Unopette™ pipette can be used to transfer 20 µl of blood into the 2 ml tube for preservation in ethanol as described above. If blood is to be held for any time prior to preservation, it should be immediately chilled in an ice water bath and then held on ice.

Feather Pulp. The proximal shaft of primary feathers that are partially grown contain a mucinous pulp rich in DNA. Feathers are best removed by a firm, steady pulling motion which insures that the feather is removed intact, without leaving a stump. The proximal 2 inches of the feather is cut, and placed in 5 ml of a pre-chilled solution of DNA Isolation Buffer (DIB -0.1M NaCl, 0.1 mM EDTA, 10 mM Tris pH 7.0). The sample in buffer should be kept on ice until it can be used for DNA preparation.

Genomic DNA Isolation

Blood. The preserved blood, which appears as very fine, reddish-brown particles, is pelleted in a microfuge tube. The ethanol is decanted and the pellet resuspended in 1 ml of cold DIB by vortexing. The blood particles are again pelleted, the liquid decanted, and the pellet resuspended in 1 ml of cold DIB. After vortexing, the solution is poured into a 15 ml polypropylene screw cap tube. The microfuge tube is then rinsed with 1 ml cold DIB, and the wash is pooled with the previous extract. 2.5 ml of cold DIB containing 0.4 mg/ml proteinase K is then added to the 15 ml tube, and the tube placed in a 60° C. water-bath for 1–5 minutes. After warming the tubes, 0.5 ml 5% SDS (sodium lauryl sulfate) is added, and the tubes are inversion. The proteinase K digestion proceeds for 2–4 hours at 60° C. The proteinase K treated preparation is then phenol extracted as specified below.

Feather Pulp. The feather pulp is removed from the feather shaft by cutting along the length of the shaft with a fine scissors, splitting the shaft open, and teasing the pulp free. The pulp is placed in a chilled mortar with approximately ½ ml of quartz sand and covered with liquid nitrogen. After the pulp is frozen and the liquid nitrogen has evaporated, the material is ground with a pestle into a powder. The powder is mixed with 2 ml DIB and poured into a 15 ml polypropylene tube. The mortar is then rinsed with another 2 ml DIB which is subsequently combined with the first extract. 0.5 ml proteinase K (2 mg/ml) is then added and the tube placed at 60° C. for 1–5 minutes. After warming, 0.5 ml of 5% SDS is added, the tubes are capped, and then mixed by gentle inverting. The proteinase K digestion proceeds for 2–4 hours at 60° C. The proteinase K treated preparation is then phenol extracted as indicated below.

After proteinase K digestion, 5 ml of Tris equilibrated phenol (pH 8.0) is added to the sample. (Phenol is equilibrated with Tris by the following procedure. Equal volumes pure phenol and 1M Tris-HCl, pH 8.0 are thoroughly mixed and allowed to separate. The Tris layer is removed and replaced with 0.1M Tris-HCl, pH 8.0 and the procedure repeated until the pH of the Tris layer is 8.0. Usually 2 or 3 changes of 0.1M Tris is required. The addition of 2 ml of 5M potassium hydroxide to the pure phenol decreases the number of extractions required.) After the addition of phenol, the samples are capped, wrapped in aluminum foil to prevent degradation of the phenol by exposure to light, and mixed thoroughly on a rocking shaker for 2–3 hours.

After shaking, the samples are incubated at 60° C. for 30 minutes in order to enhance separation of the aqueous layer, which contains phenol and denatured protein. These layers can be separated by a number of procedures: pipetting off the aqueous layer into a fresh tube, vacuum aspiration of the phenol layer, etc. A convenient method for handling large numbers of samples is to use silicon impregnated filter paper. A cone is formed from the paper and placed in a funnel. The entire sample (now at 60° C.) is poured into the cone. The paper retains the aqueous layer but allows the phenol layer to pass through. The contents of the cone are then poured back into the tube. Chloroform is then added to the sample to remove residual phenol. The sample is again gently mixed and then maintained at 4° C. for at least 2 hours. The sample is then poured into another separatory filter cone, which retains the aqueous layer but allows the chloroform to pass through. The content of the cone is then poured back into the tube.

The sample is adjusted to 0.3M sodium acetate (NaAc) by the addition of one-tenth volume of 3M sodium acetate. Two volumes of 95% ethanol are added and gently mixed with the sample. This procedure results in the extraction of water from the DNA, causing the DNA to precipitate into a white, stringy substance that can be physically picked up on a glass hook. The ethanol is poured off and the DNA on the hook is rinsed in approximately 2 ml of fresh 70% ethanol. The hook is then inverted so that the end with the DNA protrudes from the tube. The DNA sample is then allowed to air dry for several hours. The DNA is then resuspended in 400 pl of sterile TE (10 mM Tris HCl, 2 mM EDTA, pH 8.0) in 2 ml polypropylene tubes with screw caps. The samples are placed on a rocking platform shaker and permitted to dissolve. The dissolving process usually requires several days at room temperature or 24 hours at 60° C.

Generally, 20 µl of blood yields 80–120 µg of DNA resulting in concentrations of 0.2–0.3 µg/µl. Quantitation is required with feather pulp samples due to sample variability and RNA (ribonucleic acid) contamination. Quantitation is also necessary when DNA is isolated from greater volumes of blood for research purposes. 2×Pre-hybridization and 2×Hybridization Solutions

| Concentrations | Volume for 100 ml |
| --- | --- |
| 20XSSC | 50 |
| (3 M NaCl, 0.3 Trisodium citrate) | |
| 100X Denhardts* | 20 |
| 1 M Sodium phosphate pH 6.5 | 10 |
| 10 mg/ml fish sperm DNA** | 20 |

*2% each Ficoll, bovine serum albumin, poly (vinyl pyrrolidone)
**treated to reduce fragment size to an average 1000 base pairs.

This solution is filtered through paper to remove small clumps. The volume is measured and an equal volume of deionized formamide is added. Lauryl sulfate (SDS) is then added to make a 1% solution.

| | Final Concentrations |
| --- | --- |
| SSC | 5X |
| Denhardts | 10X |
| Sodium phosphate pH 6.5 | .05 M |
| Fish sperm DNA | 1 mg/ml |
| Formamide | 50% |
| SDS | 1% |

This solution is heated to 95° C. and held at 95° C. to denature the fish sperm DNA. The solution is then rapidly cooled in an ice water bath to 72° C., placed in an appropriate container, and the blots are added. The container is placed in a 42° C. shaking incubator and gently agitated for at least 8 hours.

The hybridization solution is identical to the pre-hybridization solution except for the addition of the probe. $^{32}$p labelled Tsex sequence (SEQ ID NO:1), at a concentration of 0.05 µg/ml, is used as a probe. The hybridization solution is heated to 95° C. and held at 95° C. for 5–10 minutes to denature both the fish sperm DNA and the probe DNA. The hybridization solution is then rapidly cooled to 42° C., placed in a container, and the pre-hybridized Southern blots are added. The container is incubated at 42° C. with gentle agitation for 36 hours. Blots usually require 1 ml hybridization solution per 10 cm² surface area. Usually no more than 3–4 blots are placed in the same container. Since the hybridization solution dilutes the probe, additional labeled probe must be made if more than three blots (13×15 cm) are to be hybridized.

The blots are then washed three times for 10 minutes each in 2×SSC, 0.5% SDS, at room temperature, then washed 4 times for 30 minutes each in 2×SSC and blotted dry. The damp blots are wrapped in saran wrap and placed on X-ray film between two intensifying screens. Two to four days of exposure is required to visualize hybridization bands from a single copy genes, such as Tsex. After exposure, the X-ray film is developed by the standard procedure.

Summary of Hybridization Results

A probe of SEQ ID NO: 1 was labeled and used as a hybridization probe employing the above described protocols for hybridization against chromosomal DNA preparations from numerous bird species. Table 1 provides a summary of the hybridization patterns observed for DNA samples from male and female members of the species tested. Hybridization bands are assigned to either the W chromosome, the Z chromosome, or both sex chromosomes. Blank spaces indicate the failure to test the indicated restriction endonuclease.

TABLE 1

| Hybridization Patterns (Bands in Kb) | | | | | |
|---|---|---|---|---|---|
| BamHI | EcoRI | HindIII | SacI | TaqI | Pvu II |
| Turkey W | | | | | |
| 13.5 | 9.1 | 5.7 | 5.8 | 4.2 | 3.9 |
| 7.3 | 2.3 | 5.3 | | | |
| 6.4 | | 4.4 | | | |
| 5.5 | | | | | |
| Turkey Z | | | | | |
| 19.5 | 13.5 | 6.5 | 6.3 | 5.5 | 5.4 |
| | | | 3.4 | 1.9 | 2.6 |
| Turkey | | | | | |
| nonspecific | 3.9 | | | | |
| 11.5 | 3.4 | 2.5 | 6.7 | none | 7.7 |
| Chicken W | | | | | |
| 9.7 | | 4.6 | | | |
| 4.8 | | 4.1 | | | |
| 1.65 | | | | | |
| 1.4 | | | | | |
| Chicken Z | | | | | |
| 6.1 | | 8.2 | | | |
| | | 1.7 | | | |
| Chicken | | | | | |
| nonspecific | | | | | |
| none | | 3.36 | | | |
| Pheasant W | | | | | 8.5 |
| | | | | | 7.6 |
| | | | | | 6.6 |
| Pheasant Z | | | | | 5.1 |
| | | | | | 3.6 |
| | | | | | 2.95 |

TABLE 1-continued

| Hybridization Patterns (Bands in Kb) | | | | | |
|---|---|---|---|---|---|
| BamHI | EcoRI | HindIII | SacI | TaqI | Pvu II |
| Canada W Geese | | | | | |
| 13 | | | | | |
| 7.7 | | | | | |
| Canada Geese Z | | | | | |
| 21 | | | | | |
| 14.5 | | | | | |
| Orange Wing Amazons W | | | | | |
| 7.1 | | 15.2 | | | |
| Orange Wing Amazons Z | | | | | |
| 14.3 | | 4.8 | | | |
| 8.6 | | | | | |
| Cockatiel W | | | | | |
| 12.6 | | 7.1 | | | |
| Cockatiel Z | | | | | |
| 20.1 | | 8.1 | | | |
| Conures Band Z | | 4.6 | | 1.7 | |
| Lovebirds Z Band | 8.1 | 7.3 | 6.4 | 2.2 | |
| | | | | 1.85 | |
| African Gray Parrot Z Band | 5.0 | 5.4 | 1.75 | 3.9 | |
| | | | | 3.2 | |
| Yellow Collar Macaws Z | | | | | 7.75 |
| Yellow Collar Macaws W | | | | | 5.9 |
| Blue & Gold | | | | | 6.3 |
| Macaws Z Blue & Gold | | | | | 4.8 |
| Macaws W Hyacinth | | | | | 7.7 |
| Macaw Z Hyacinth | | | | | 6.3 |
| Macaw W Scarlet Macaw Z | | | | | 7.3 |
| Scarlet Macaw W | | | | | 5.7 |

EXAMPLE 2

PCR amplification of a female specific fragment using Tsex

The following reaction was set up:

| | |
|---|---|
| genomic DNA | 25 ng |
| 10X PCR buffer | 5 µl |
| 25 mM MgCl2 | 7 µl |
| dNTP (2.5 mM each) | 5 µl |
| *Primer 1 (100 ng/ul) | 0.5 µl |
| **Primer 2 (100 ng/ul) | 0.5 µl |
| Taq Polymerase (5 U/ul) | 0.2 µl |
| Distilled water | to volume of 50 µl |

*Primer 1 consists of an oligonucleotide primer of SEQ ID NO: 3.
**Primer 2 is an oligonucleotide primer consisting of bases 933–955 of SEQ ID NO: 2: (GTGTCTGCCACAGCATCTGATG)

The following parameters were used for the polymerase chain reaction: 1 cycle at 95° C., 1 minute; 35 cycles at 95° C., 15 seconds; 55° C., 30 seconds; 72° C., 75 seconds; 1 cycle at 72° C., 10 minutes; 1 cycle at 4° C., hold.

Following amplification, resulting fragments are separated by agarose gel electrophoresis and visualized by staining with ethidium bromide. Gels are photographed for documentation.

The combination of a primer from SEQ ID NO:2 and SEQ ID NO:3 allows specific amplification of fragments from the W chromosome, detectable only in females. SEQ ID NO:3 is exemplary of an intron sequence that is specific to the W chromosome of many avian species.

EXAMPLE 3

Identification and Characterization of an Ostrich Sex Specific Sequence

A tetranucleotide repeat, $(GACA)_4$ oligonucleotide sequence was end-labeled and used as a probe to screen a size selected female ostrich genomic library. A clone hybridizing to the $(GACA)_4$ sequence was isolated and partially sequenced. A non-repetitive BamHI fragment from the 3' end of the clone was radiolabeled, and demonstrated to generate a sex specific pattern when hybridized to Southern blots of HaeIII digests of ostrich genomic DNA. Oligonucleotide primers designed from the sequence of the clone were utilized in the PCR to amplify sex specific sequences from ostrich genomic DNA. A partial sequence of the 4.8 Kb HaeIII fragment isolated from the library is listed SEQ ID NO:4.

The accuracy of gender identification by RFLP with the provided probe sequence was examined. Genomic DNA from 80 birds of known sex was digested with HaeIII and fractionated by size on 0.8% agarose gels. The DNA was denatured and blotted onto nylon membranes, prehybridized, and hybridized with the radiolabelled 534 bp BamHI fragment. The membranes were washed and exposed to X-ray film. The genetic sex as determined by the RFLP procedure was identical to the phenotypic sex of every bird.

The accuracy of sex determination using the provided oligonucleotide primers for the PCR was also studied. After appropriate reaction conditions were established for analysis of ostrich genomic DNA by PCR, PCR reactions were performed on genomic DNA from 80 birds of known phenotypic sex. In every case, the genetic sex as assayed by the PCR matched the phenotypic sex.

Identification and Cloning of a Sex Specific RFLP. In order to create a DNA fingerprint, female and male ostrich genomic DNAs were digested to completion with HaeIII and size fractionated on a 0.8% agarose gel. DNA was transferred onto a nylon membrane according to the manufacturer's protocols, and the membrane was baked at 80° C. for one hour to dry. The membrane was exposed to UV light on a standard UV transilluminator for two minutes, and then was prehybridized in 0.5M Sodium Phosphate pH 7.0, 7% SDS and 5mM EDTA for 30 minutes at 42° C. It was hybridized overnight with $^{32}p$ end labeled $(GACA)_4$ oligonucleotide. It was washed for one hour at room temperature in 2×SSC and 0.1% SDS, then for 30 minutes at 42 ° C. in 1×SSC and 0.1% SDS and exposed to X-ray film overnight at −80° C. using an intensifying screen. Upon examination of the autoradiogram, it was noted that a band of approximately 4.8 Kb in size (as determined by comparison with lambda HindIII molecular weight markers) appeared in all lanes containing female DNA, but not in any lanes containing male DNA. Because the autoradiogram also contained many other bands of similar size, it was not particularly suited for accurate sex determination. A unique single or low copy sequence would be superior.

The 4.8 Kb HaeIII female ostrich fragment hybridizing to the $(GACA)_4$ oligonucleotide was therefore cloned. A library of female ostrich fragments was constructed in λgt11 according to the following procedure. Several female ostrich DNAs were selected whose fingerprint exhibited few other bands in the region of interest. The DNAs were digested to completion with HaeIII and fractionated by size on a 0.8% agarose gel. Gel slices corresponding to DNA of about 4.5 to 5.2 Kb in size were isolated, and the DNA was purified from the agarose using the GeneClean Kit (Bio101, Vista, Calif.). One mg blunt/sticky end hemiphosphorylated NotI/ EcoRI adaptors (Invitrogen, San Diego, Calif.) were ligated to 250 ng of the ostrich HaeIII fragment in a volume of 20 ml overnight at 14° C. The ligation was then extracted once with an equal volume of phenol:chloroform (1:1) and DNA was precipitated with 0.15 volumes of 2M sodium acetate and 2 volumes of 95% ethanol. DNA was washed with 70% ethanol, dried, and resuspended in water. T4 Polynucleotide kinase was employed in a 20 ml reaction to phosphorylate the ends of the DNA fragments for ligation into λgt11. The kinase was heat inactivated at 70° C. for five minutes, and the DNA was size fractionated on a low melting point agarose gel for removal of adaptors. The 4.8 Kb fragment was excised and purified from the gel using beta agarase (NEB, Beverly, Mass.). Half of the recovered DNA was ligated to 500 ng λgt11 EcoRI arms (Promega, Madison, Wis.) in a five ml volume for three hours at room temperature. The DNA was packaged using GigaPack II Plus packaging extract (Stratagene, La Jolla, Calif.) according to the manufacturer's instructions, and was transfected into Y1090 cells.

The resultant library, containing 100,000 primary recombinants, was plated onto three 15 cm Petri plates for screening with the $^{32}p$ end labeled $(GACA)_4$ oligonucleotide. Nitrocellulose membranes pre-wet in 2×SSC were placed onto the plates and rubbed gently to ensure contact with plaques. Membranes were transferred to a solution containing 100 mM NaOH and 1.5M NaCl for 70 seconds with rocking, and then removed to 2×SSC, 0.1M $NaH_2PO_4$, 0.2M Tris-Cl, pH 7.2 for 10 minutes with rocking. Membranes were baked dry for one hour at 80° C. and then exposed to UV light for two minutes. They were prehybridized in 0.5M Sodium Phosphate pH 7.0, 7% SDS and 5 mM EDTA for 30 minutes at 42° C. They were hybridized overnight with $^{32}p$ end labeled $(GACA)_4$ oligonucleotide at 42° C., then washed for one hour at room temperature in 2×SSC and 0.1% SDS, for one hour at 42° C. in 1×SSC and 0.1% SDS and exposed to X-ray film overnight at −80° C. using an intensifying screen. Five plaques hybridizing with the $(GACA)_4$ oligonucleotide were subjected to a secondary screen using the same procedure. Two of the chosen plaques hybridized upon secondary screening, and these were further purified by a tertiary screen.

Confirmation of Identity of the Cloned DNA. DNA was isolated from one of the recombinant phage (designated O2a) by a fast and simple protocol (BioTechniques 14(3):360–361). The phage DNA was digested with NotI to release the 4.8 Kb fragment, which was then labeled with $^{32}p$ and used for hybridization to Southern blots of ostrich genomic DNA digested with HaeIII. The probe hybridized to the 4.8 Kb HaeIII fragment in female but not in male ostrich DNA, confirming the identity of the cloned DNA. However, the hybridization pattern was still unsatisfactory for commercial sex determination, yielding numerous irrelevant bands, perhaps due to repetitive sequence contained in the clone.

Characterization of the 4.8 Kb HaeIII Fragment. The 4.8 Kb NotI fragment released from the phage DNA was subcloned into pBluescript (Stratagene, La Jolla, Calif.) for further analysis. It was sequenced in the 5' and 3' directions with T7 and T3 primers, respectively, using the Sequenase kit (USB). The 5' end of the clone contained very repetitive sequence, and was not of immediate interest, since the 3' end consisted of apparently non-repetitive sequence. A total of about 700 bp of the 3' end of the clone was sequenced (SEQ ID NO:4), and it was observed on the autoradiograms of the sequencing gels that there was highly repetitive sequence present farther in the 5' direction (the first 20 bp of the provided sequence indicates the start of the repetitive sequence).

In order to obtain additional information about the interior of the sequence, a restriction map of the clone was made using BamHI, EcoRI, HindIII, PstI, PvuII, SacI, SalI, TaqI, and XbaI. Out of all of the enzymes tested, the cloned fragment only possessed a single BamHI site located approximately 500 bp from the 3' end and a single TaqI site in close proximity to the BamHI site. The lack of restriction sites (especially the dearth of TaqI sites, since it is a 4-cutter) in such a large fragment suggested that the majority of the clone, excluding only the 3' end, consisted of extremely repetitive sequence.

Construction and Testing of a Probe for Sex Determination by RFLP. Since it was likely that most of the clone was repetitive, the non-repetitive 534 bp BamHI fragment (SEQ ID NO:4, nt 174–710) generated from the internal and plasmid BamHI sites seemed an appropriate choice for a single copy sequence to use as a probe for sex determination by RFLP. The plasmid containing the 4.8 Kb clone was digested to release the BamHI fragment, which was then subcloned into the BamHI site of pBluescript (Stratagene, La Jolla, Calif.). The probe was synthesized by labeling the BamHI fragment with $^{32}$p by random priming using the MultiPrime DNA Labeling System (Amersham, Arlington Heights, Ill.).

Genomic DNA from 80 ostriches of known sex was digested with HaeIII and fractionated by size on a 0.8% agarose gel. DNA was transferred to nylon membranes which were baked and prehybridized as above, except that the temperature was 65° C. Hybridization was performed with the labeled BamHI fragment, also at 65° C. overnight. The membranes were washed once at room temperature in 2×SSC and 0.1% SDS, then once for 30 minutes at 55° C. in 0.2×SSPE and 0.5% SDS. They were exposed to X-ray film overnight, as above. The hybridization patterns revealed a band of about 650 bp in all lanes, and a band of 4.8 Kb in every lane containing female DNA but not in lanes with male DNA. This probe thus fulfilled the desired criteria of hybridizing to a single copy ostrich sequence diagnostic of sex.

Design and Implementation of Oligonucleotide Primers for Sex Determination by PCR. The sequence, restriction map and RFLP information gathered suggested that much of the 4.8 Kb HaeIII fragment cloned from female ostrich was repetitive, and the RFLP results implied that this repetitive sequence was not present in the male genome in its entirety. It was hypothesized that an oligonucleotide primer for PCR designed immediately adjacent to the repetitive DNA sequence might yield female specific amplification products. In addition, an oligonucleotide sequence at the 3' end of the clone might be present in male and female DNAs, since the BamHI fragment hybridized to a 650 bp fragment in DNAs from both sexes. Oligonucleotides 2A-1 and 2A-6 were designed and ordered (Operon Technologies, Alameda, Calif.).

PCR was performed on genomic DNAs from birds of known sex under the following conditions: 25 ng genomic DNA, 50 ng primer 2A-1, 50 ng primer 2A-6, 50 mM KCl, 10 mM Tris-Cl pH 8.3, 3 mM MgCl2, 250 mM each dNTP, 1 unit AmpliTaq DNA polymerase (Perkin Elmer, Norwalk, CT) in a 50 ml reaction volume. Cycling parameters were 1 cycle of 94° C. for 1 minute, 30 cycles of 94 ° C for 15 seconds, 55° C. for 15 seconds, and 72° C. for 75 seconds, followed by 1 cycle of 72° C. for 10 minutes in a GeneAmp 9600 thermocycler (Perkin Elmer, Norwalk, Conn.). Using this procedure, a band of about 600 bp was amplified from all female DNAs but not from any male DNAs. The only difficulty with this procedure is that it would be impossible to distinguish a failed PCR reaction from a reaction containing male DNA.

To circumvent this problem, a technique called low stringency PCR was utilized. Low stringency PCR uses specific primers but at a lower annealing temperature to attempt to generate some non-specific bands in addition to the desired specific PCR product (Neto et. al, Nuc. Acids Res. 21(3) :763–764). With this in mind, PCR was performed according to the above conditions, except that the annealing temperature was reduced to 41° C. Using these conditions, 80 genomic DNAs from ostriches of known sex were amplified. A band of about 1.5 Kb amplified from both male and female DNA, whereas a band of about 600 bp amplified only from female DNA. The 1.5 Kb amplified DNA acted as an ideal control for the presence and quality of DNA in the PCR reaction, distinguishing between failed PCR reactions and reactions containing male DNA.

Preparation of Ostrich Genomic DNA from Blood Samples

For RFLP Analysis. Whole blood is collected in two 20 ml heparinized glass hematocrit tubes. The tube is placed in a vial with 1.5 ml 70% ethanol; the blood sample is stable in the ethanol for several weeks at ambient temperature. Samples are centrifuged at 2000 rpm in a tabletop centrifuge for five minutes. The supernatant and hematocrit tubes are discarded and the pellet resuspended in 0.1M NaCl, 0.05M Tris-HCl pH 8.0, 0.1M EDTA, 0.5% SDS and 0.2 mg/ml Proteinase K. The tubes are heated in a water bath for 10 minutes at 55°–65° C. and then rocked gently in an incubator for 3 hours at 55° C.

Following the incubation, 0.5 ml of saturated NaCl is added and the samples shaken vigorously for 30 seconds. They are then centrifuged for 15 minutes at 2000 rpm in a tabletop centrifuge, and the supernatant decanted into a fresh tube. Three ml of 95% ethanol is added to the supernatant, and the solution is gently mixed until the DNA precipitate is formed. The precipitate is removed with a glass hook made from a Pasteur pipette, rinsed in 70% ethanol, an allowed to air dry. The DNA is then resuspended in 0.75 ml TE (10 mM Tris-HCl pH 8.0, 2 mM EDTA).

For PCR Analysis. Method 1; blood is collected as for RFLP analysis, and the tube containing ethanol and blood is shaken vigorously. 200 ml of the solution is aliquotted into a 1.5 ml microfuge tube. The tube is centrifuged at maximum speed in a microfuge for 15 seconds, and the supernatant carefully removed. The pellet is resuspended in 200 ml 1×PBS and then DNA is prepared according to the manufacturer's protocol (Qiagen, Chatsworth, Calif.) beginning with the step calling for the addition of 25 ml of Protease solution. Five to ten ml of the resultant DNA is used for the PCR.

Method 2; blood is collected as for RFLP analysis, and the tube containing ethanol and blood is shaken vigorously. Approximately 200 ml of the solution is poured into a 1 ml microtiter tube (Bio-Rad, Hercules, Calif.). The solution is allowed to settle for 15 minutes, and then 1 ml of the solution is placed into a PCR tube. The PCR tube is incubated open for 10 minutes at 55° C. to allow the ethanol to evaporate. Five ml of lysis buffer (10 mM Tris-HCl pH 8.3, 50 mM KCl, 2.5 mM MgCl2, 0.45% NP-40) is added to the PCR tube, along with 5 ml of 7 mg/ml protease (Qiagen, Chatsworth, Calif.). The PCR tube is placed in an oil free thermocycler and heated to 55° C. for 15 minutes, followed by 10 minutes at 95° C. All 10 ml of the DNA solution is then used for the PCR.

DNA Preparation from Feather Shafts. Feathers from adult ostrich are collected. The tip of the feather shaft is cut off and placed into a PCR tube. Fifty ml of lysis buffer (see above) plus 1 mg/ml protease (Qiagen, Chatsworth, Calif.) is added to the tube, which is then incubated in an oil free thermocycler for 1 hour at 55° C. and 10 minutes at 95° C. Ten ml of the DNA solution is then used for the PCR.

EXAMPLE 4

Identification and Characterization of an Emu Sex Specific Sequence

Utilizing bulked segregant analysis (described in Michelmore et. al., (1991) *Proc. Natl. Acad. Sci.* 88(21):9828–32) and RAPD techniques (described in Williams et. al. (1990) *Nucleic Acids Res.* 18:6531–6535), a sex specific DNA fragment amplified by a 10-mer oligonucleotide primer was isolated from emu DNA. The DNA fragment was cloned and sequenced, and two longer oligonucleotide primers (16E-1 and 16E-3) were designed that produce a female specific DNA fragment in high stringency PCR. A third oligonucleotide primer (16E-1125) was designed opposing the 5' oligonucleotide primer for ease of use in sex identification on a commercial basis. A single copy sequence for use as a sex determination probe in RFLP was also designed from the original sex specific DNA fragment.

The sequence of the sex specific DNA fragment isolated by bulked segregant and RAPD analysis is provided in SEQ ID NO:5. The fragment is named 16E-1200bp after the 10-mer oligonucleotide used to generate the fragment in RAPD analysis.

The accuracy of sex determination using the provided oligonucleotide primers for the PCR was studied. After appropriate reaction conditions were established for analysis of emu genomic DNA via the PCR with primers 16E-1 and 16E-3, PCR reactions were performed on genomic DNA from 48 birds of known phenotypic sex to confirm the accuracy of sex determination by this procedure. Later, after development of sex determination procedures using primers 16E-3 and 16E-1125, an additional 52 birds of known phenotypic sex were analyzed using those primers in a blind study to determine their genetic sex. The phenotypic sex matched the genotypic sex as determined by PCR in all 100 of the birds studied.

The accuracy of gender identification by RFLP with the provided probe sequence was also examined. Sex was determined by PCR with primers 16E-3 and 16E-1125 of a random selection of 500 emu DNA samples and subsequent agarose gel electrophoresis of the amplified DNAs. RFLP analysis was then conducted on the 500 genomic DNAs. They were digested, fractionated by size on agarose gels, blotted onto nylon membranes, prehybridized and hybridized with the provided probe. The membranes were washed and exposed to X-ray film. The sex as determined by this RFLP procedure agreed with the sex obtained by the PCR procedure in each of the 500 birds.

The provided oligonucleotide sequences can be used to generate an amplified DNA in the PCR that is specific to female emus. When the PCR is performed with primers 16E-3 and 16E-1125 at low stringency as described in the examples, additional DNAs common to male and female are also amplified.

The provided sequence for a probe is employed to generate single locus RFLPs that are specific to females. When the RFLP is obtained using the enzymes described, an additional band common to males and females is observed; this band also acts as an internal control for the presence and quality of DNA in each lane.

Identification and Characterization of a Female Specific RAPD. Roughly equal amounts of genomic DNA from ten female emus and ten male emus was combined into two pools for bulked segregant analysis. PCR reactions were performed on each pool with 25 ng DNA, 100 mM each dNTP, 10 mM Tris-HCl pH8.3, 50 mM KCl, 1.5 mM MgCl2, 0.001% Gelatin, 1 unit AmpliTaq polymerase (Perkin Elmer, Norwalk, Conn.) and 30 ng of one random 10-mer oligonucleotide primer (Operon Technologies, Alameda, Calif.) per 25 ml reaction. Over 400 primers were used in over 800 PCR reactions. The PCR reaction conditions to generate RAPDs were as follows: 1 cycle of 94° C. for 30 seconds, 40 cycles of 94° C. for 1 minute, 35° C. for 1 minute, and 72° C. for 2 minutes, and 1 cycle of 72° C. for 10 minutes. The entire PCR reaction was size fractionated on a 1.5% agarose gel, which was stained and photographed. DNA fragments amplified from the female DNA pool but not the male DNA pool were cut out of the gel, and the gel slices were stored at 4° C. for later use.

To confirm female specificity of an amplified DNA, identical PCR reactions were performed individually on twenty additional male and female DNAs utilizing the same 10-mer oligonucleotide as a primer. This was necessary because some fragments appeared female specific in the pooled DNA reaction but later amplified in some male individuals. A 1.2 Kb fragment amplified using primer 16E was female specific in the pooled DNA and also in additional reactions performed on individual emu DNAs. The fragment was then isolated from the original gel slice using the GeneClean Kit (Bio 101, Vista, Calif.) and resuspended in a total volume of 10 ml. Five ml of this DNA was re-amplified in a PCR with the 16E primer under the above conditions to generate sufficient material for subcloning. The re-amplified fragment was cloned into pCRII using the TA Cloning Kit (Invitrogen, San Diego, Calif.). An equimolar amount of fragment was ligated to 50 ng of prepared pCRII vector in a 10 ml ligation reaction and was incubated at 15° C. overnight, all according to kit instructions. Ligations were then transformed into One Shot chemically competent cells (Invitrogen, San Diego, Calif.) and plated onto LB-ampicillin plates containing X-gal. White colonies were selected and plasmid DNA was prepared from overnight cultures by the alkaline lysis miniprep procedure. Plasmid DNAs were digested with EcoRI to release the inserts, and three clones were found to contain a 1.2 Kb insert. These were sequenced using the Sequenase kit (USB) and found to contain the provided 1236 bp nucleotide sequence.

To firmly establish the identity of the cloned DNA fragments, 44 individual emu genomic DNAs (23 male and 21 female) were amplified by the PCR using the RAPD conditions with the 16E 10-mer oligonucleotide primer and fractionated on a 1.5% agarose gel. The cloned 1.2 Kb insert was radiolabeled with $^{32}p$ by random priming using the Multiprime DNA Labeling System (Amersham, Arlington Heights, Ill.), and the extent of hybridization with the amplified DNAs monitored by Southern blot. None of the male derived amplified DNAs showed hybridization to the probe, and all but three of the female derived amplified DNAs hybridized strongly. The three non-hybridizing female DNAs were later determined to be degraded.

Amplification of Genomic DNA with SCAR Primers. Oligonucleotide primers containing the 16E primer sequence and additional flanking sequence were designed (primers 16E-1 and 16E-3). PCR was performed under the following conditions: 25–250 ng emu genomic DNA, 100 ng 16E-1 primer, 100 ng 16E-3 primer, 250 mM each dNTP, 2.0 mM MgCl$_2$, 60 mM Tris-HCl, 15 mM (NH$_4$)$_2$SO$_4$, and 1 unit AmpliTaq DNA polymerase per 50 ml reaction. DNAs were amplified by 1 cycle of 94° C. for 1 minute, 30 cycles of 94° C. for 1 minute, 55° C. for 1 minute, and 72° C. for 1 minute, followed by 1 cycle of 72° C. for 10 minutes. PCR products were analyzed by size fractionation on 1.0% agarose gels. Using this procedure, a 1.2 Kb fragment was amplified in female but not in male emus.

One inherent problem with this procedure was the lack of a positive control for the reaction; it would be difficult to distinguish failed PCR reactions from reactions containing male DNA. For this reason, a method called low stringency PCR was adopted, as described for the ostrich sequence. PCR was performed according to the above conditions, except that the annealing temperature was reduced to 45° C. Using these conditions, 48 genomic DNAs from emus of known sex were amplified. A band of about 700 bp was amplified from male and female emu DNA, and a 1.2 Kb band was visualized in females only. However, since competition for reaction components might favor production of the smaller and more easily amplified DNA, there was the possibility that the 700 bp band but not the 1.2 Kb band might amplify when using this procedure on female DNA of poor quality or in less than optimal reaction conditions. A more desirable assay would produce a female specific PCR product that was of a lesser size than the non-specific products, and would also only generate fragments under 1 Kb in size to increase the probability of obtaining amplified product even from partially degraded DNA samples.

To this end, various PCR primers were designed along the length of the 16E-1200 bp clone. It was noted that while PCR performed with the 16E-3 primer and any opposing primer yielded female specific bands, reactions carried out with 16E-1 and opposing primers did not. Therefore, 16E-3 and various opposing primers were tested in low stringency PCR to attempt to locate an opposing primer which, in conjunction with 16E-3, would generate a small size female specific PCR product in addition to larger non-specific control bands. Primer 16E-1125 in combination with primer 16E-3 was found to amplify PCR products with the desired qualities. A female specific fragment of 399 bp is amplified, in addition to non-specific bands of larger size. All of the amplified products are smaller than 1 Kb. The PCR conditions resulting in the most consistent amplification in a GeneAmp 9600 thermocycler (Perkin Elmer, Norwalk Conn.) are: 1 cycle of 94° C. for 1 minute, 30 cycles of 94° C. for 15 seconds, 41° C. for 15 seconds, and 72° C. for 75 seconds, and 1 cycle of 72° C. for 10 minutes. The reaction components are 25 ng genomic DNA, 50 ng primer 16E-3, 50 ng primer 16E-1125, 250 mM each dNTP, 50 mM KCl, 10 mM Tris-Cl pH 8.3, 3.0 mM MgCl2, and 1 unit of AmpliTaq DNA polymerase (Perkin Elmer, Norwalk, Conn.) in a 50 ml reaction volume. PCR products were size fractionated on 2% agarose gels to facilitate complete separation of small fragments of similar size.

Once optimal conditions for sex identification of emus by PCR were determined, 52 additional genomic DNAs from birds of known sex were analyzed by PCR in a blind study. After size fractionation on agarose gels, the genotypic sex was determined by scoring each lane for presence or absence of the 399 bp female specific PCR product. Once the results were obtained, they were compared with the phenotypic sex of the birds. The phenotypic and genotypic sex matched for every bird tested.

Development of a Probe for Detecting a Female Specific RFLP

Synthesis of a Probe Based on the 16E-1200 bp Sequence. For commercial purposes, it was desirable to have an alternate method for sex determination in emus for use as a backup.

Using PCR primers described above, a fragment was amplified from the cloned 16E-1200 bp sequence. Fragment 16EP6 spanned nt 563–1236 in SEQ ID NO:5. The fragment was fractionated on an agarose gel to determine approximate concentration relative to a standard, and diluted to 5 ng/ml for labeling with $^{32}$p using the Multiprime DNA Labeling System (Amersham, Arlington Heights, Ill.).

RFLP Analysis. Genomic DNA from 43 emus of known sex was digested with TaqI and size fractionated on 0.8% agarose gels. DNA was transferred onto nylon membranes according to the manufacturer's protocols, and membranes were baked at 80° C. for 1 hour to dry. The membranes were exposed to UV light on a standard UV transilluminator for two minutes, and then membranes were prehybridized in 0.5M Sodium Phosphate pH 7.0, 7% SDS, and 5 mM EDTA for 30 minutes at 65° C. They were hybridized with the 16EP6 probe overnight at 65° C. They were washed in 2×SSC and 0.5% SDS for 15 minutes at room temperature, followed by a thirty minute wash at 55° C. in 0.2×SSPE and 0.5% SDS. They were then blotted dry on Whatman 3 mm paper and exposed to X-ray film overnight at −80° C. using an intensifying screen.

Some of the genomic DNAs were of poor quality, so results were obtained for only 26 of the digested DNAs. The 16EP6 probe hybridized to DNAs of approximately 6600 bp in all birds tested, and hybridized to DNAs of about 4500 bp in female samples only. Based on these results, 500 genomic DNAs from emus whose gender had previously been determined by PCR with primers 16E-3 and 16E-1125 were digested with TaqI and subjected to the remainder of the RFLP analysis procedure above. Gender was scored based on whether or not hybridization of 16EP6 to the 4500 bp TaqI fragment was observed. The gender was then compared to the earlier result obtained by PCR. In every case, the sex obtained by RFLP analysis was identical to that determined by PCR.

Emu genomic DNA was prepared for analysis as described for ostrich DNA, except that double shafted feathers from adult emu are collected. The double feathers are pulled apart and the tip of the feather shaft is cut off and placed into a PCR tube.

Table of Primers for Amplification Reactions

| Lab designation | SEQ ID NO | Sequence |
| --- | --- | --- |
| Tsex nt 933–955 | SEQ ID NO: 6 | GTGTCTGCCACAGCATCTGATG |
| (GACA)₄ | SEQ ID NO: 7 | GACAGACAGACAGACA |
| 2A-1 | SEQ ID NO: 8 | CCTTGTATCTTCACTCTAGA |
| 2A-6 | SEQ ID NO: 9 | TCTCTGAGGATTCACTGTTC |
| 16E-1125 | SEQ ID NO: 10 | TGTATCTAGCGTGGGATTTCAGTTG |
| 16E-1 | SEQ ID NO: 11 | GGTGACTGTGGTGACTGTGGACAAG |
| 16E-3 | SEQ ID NO: 12 | GGTGACTGTGCTAGCTAATAACTACG |
| Tsex L9-3 | SEQ ID NO: 13 | GTATCTATGTTGCTATTGGC |
| Tsex L9-4 | SEQ ID NO: 14 | CAGAGACATCTGACGATAGG |
| Tsex JH-2 | SEQ ID NO: 15 | GCTGGGCTCCAGCTTGTCC |
| Tsex JH-7 | SEQ ID NO: 16 | GCTGGTACCATGAAGCTGG |

It is evident from the above results that simple, accurate and efficient methods are provided for determining the sex of birds at a stage when visual manifestations of sex characteristics are not apparent. In this manner, matings may be accurately made and other events associated with the sex of the bird may be properly performed.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated nucleic acid for the identification of sex in avian species, consisting of a sequence selected from the group consisting of SEQ ID NO:3; and SEQ ID NO:5, or the complementary sequence thereof or a fragment of at least eighteen nucleotides thereof.

2. An oligonucleotide primer comprising a fragment of at least eighteen contiguous nucleotides of a sequence of claim 1, or said fragment joined to a label.

3. A primer according to claim 2, wherein said primer is joined to a radiolabel, biotin, an enzyme, a fluorescer or a chemiluminescer.

4. A replication vector comprising at least eighteen contiguous nucleotides of the sequence of claim 1.

5. A kit for use in avian sex identification comprising:

a pair of oligonucleotide amplification primers of at least eighteen nucleotides, wherein the sequence of said pair of oligonucleotide primers is selected from within the sequence of SEQ ID NO:2 in combination with SEQ ID NO:4 or SEQ ID NO:5.

6. A kit according to claim 5, wherein the sequence of said oligonucleotide amplification primers is selected from the group consisting of SEQ ID NO:6 and 3; 13 and 3; 14 and 3; 15 and 3; 16 and 3; 8 and 9; and 10 and 12.

7. A method for determining whether an avian chromosomal DNA sample is from a male or female bird; wherein said bird is characterized by having a specific sequence on at least one of the sex W and Z chromosomes unique to the sex chromosome, said sequence being within the sequence selected from the group consisting of SEQ ID NO:2; SEQ ID NO:4 and SEQ ID NO:5;

said method comprising:

preparing said avian chromosomal DNA sample for hybridizing or, when the distinction in sex is based on difference in restriction fragment length polymorphisms, a) digesting said avian chromosomal DNA sample with at least one restriction endonuclease; and b) size separating said restriction endonuclease digested DNA;

hybridizing said avian chromosomal DNA sample with a primer capable of specifically hybridizing to nulceotides 1-941 of SEQ ID NO:2; SEQ ID NO:4, or SEQ ID NO:5, or the complementary sequence thereof or a fragment of at least eighteen nucleotides thereof and determining the presence, size and/or intensity of hybridizing bands as indicative of the sex of the bird.

8. A method according to claim 7, wherein said primer is labeled with a label capable of providing a detectable signal.

9. A method according to claim 7, wherein said sequence is on both the Z and W chromosomes and said determining is by size.

10. A method according to claim 7, wherein said sequence is on either the Z or W chromosome and said determining is by measuring the intensity of a labeled sized fragment.

11. A method according to claim 10, wherein said sized fragment is separated by gel electrophoresis.

12. A method for determining whether an arian chromosomal DNA sample is from a male or female bird, wherein said bird is characterized by having a specific sequence on at least one of the sex W and Z chromosomes unique to the sex chromosome, the method comprising:

amplifying said avian chromosomal DNA sample with a pair of oligonucleotide amplification primers of at least eighteen nucleotides, wherein the sequence of said pair of oligonucleotide primers is selected from within the sequence of SEQ ID NO:4; or SEQ ID NO:5 or SEQ ID NO:2 in combination with SEQ ID NO:3;

wherein the presence of an amplification product is indicative that said arian chromosomal DNA sample is from a female bird.

13. A method according to claim 12, wherein said amplification is by polymerase chain reaction.

14. A method according to claim 13, wherein the sequence of one of said amplification primers is selected from within the sequence of SEQ ID NO:2, and the sequence of one of said amplification primers is SEQ ID NO:3.

15. A method according to claim 13, wherein said amplification is by low stringency polymerase chain reaction, and wherein an additional amplification product common to male and female birds is produced.

16. A method according to claim 13, wherein the sequence of said amplification primer is selected from within the sequence of SEQ ID NO:4.

17. A method according to claim 16, wherein the sequence of said amplification primers is SEQ ID NO:8 and SEQ ID NO:9.

18. A method according to claim 13, wherein said bird is an emu, and said pair of oligonucleotide primers is selected from with the sequence of SEQ ID NO:5.

19. A method according to claim 18, wherein the sequence of said amplification primers is SEQ ID NO:10 and SEQ ID NO:12.

20. An isolated nucleic acid for the identification of sex in avian species consisting of a sequence selected from the group consisting of nucleotides 1-941 of SEQ ID NO:2 and SEQ ID NO:4, or the complementary sequence thereof or a fragment of at least 35 nucleotides thereof.

21. An oligonucleotide primer comprising a fragment of at least 35 contiguous nucleotides of a sequence of claim 20, or said fragment joined to a label.

22. A primer according to claim 21, wherein said primer is joined to a radiolabel, biotin, an enzyme, a fluorescer or a chemiluminescer.

23. A replication vector comprising at least 35 contiguous nucleotides of the sequence of claim 20.

* * * * *